United States Patent
Khazaka

Patent Number: 5,935,521
Date of Patent: Aug. 10, 1999

[54] MEASURING SYSTEM FOR DETERMINING THE SECRETION OF SEBUM FROM THE SKIN

[75] Inventor: Gabriel Khazaka, Cologne, Germany

[73] Assignee: Courage + Khazaka electronic GmbH, Cologne, Germany

[21] Appl. No.: 08/875,889

[22] PCT Filed: Feb. 23, 1996

[86] PCT No.: PCT/EP96/00749

§ 371 Date: Aug. 6, 1997

§ 102(e) Date: Aug. 6, 1997

[87] PCT Pub. No.: WO96/25884

PCT Pub. Date: Aug. 29, 1996

[30] Foreign Application Priority Data

Feb. 24, 1995 [DE] Germany ............ 295 03 080 U

[51] Int. Cl.⁶ .................................................. G01N 33/48
[52] U.S. Cl. ............................. 422/61; 604/1; 436/63; 436/164
[58] Field of Search ............. 422/58, 61; 604/1–2, 604/322; 436/63, 164, 165

[56] References Cited

U.S. PATENT DOCUMENTS

| 4,483,619 | 11/1984 | Leveque et al. | 356/434 |
| 5,119,828 | 6/1992 | Miller | 128/760 |

FOREIGN PATENT DOCUMENTS

| 2063743 | 7/1971 | France . |
| 3213944 | 10/1983 | Germany . |
| 91/06242 | 5/1991 | WIPO . |
| 93/14699 | 8/1993 | WIPO . |

Primary Examiner—Lyle A. Alexander
Attorney, Agent, or Firm—Diller, Ramik & Wight, PC

[57] ABSTRACT

The invention concerns a measuring device for determining the secretion of the sebum from the skin using a microporous, water-repellent, sebum-absorbing opaque foil (4) which, on contact with the skin, can absorb sebum secreted by the surface of the skin, the transparency of the foil (4) being a measure of the absorbed sebum. In the edge region the sebum-absorbing foil (4) is attached to a carrier (2) which is provided with a window or is transparent in the area of the foil (4) to be brought into contact with the surface of the skin.

8 Claims, 1 Drawing Sheet

MEASURING SYSTEM FOR DETERMINING THE SECRETION OF SEBUM FROM THE SKIN

The invention relates to a device for collecting the secretion of sebum from skin.

BACKGROUND OF THE INVENTION

Such collecting or measuring systems are required to assess the amount and the distribution of the secretion of sebum from the skin by measurement. From U.S. Pat. No. 5,119,828, the use of a microporous hydrophobic sebum absorbing opaque film is known, the pores of which can fill with sebum from the skin when in contact with the skin, whereby they can make the initially opaque film transparent to light. The film has rigid paper adhered thereto, which is black in the contact area of the film on the skin. It is a disadvantage of such a collecting or measuring system that the paper accommodating the film will be kinked upon application, whereby the optical evaluation of the skin print on the film is made more difficult or falsified.

SUMMARY OF THE INVENTION

It is an object of the present invention to provide an improved collecting or measuring means for determining the secretion of sebum from the skin, wherein the reproducibility of the measuring values is improved and the evaluation is facilitated.

The invention advantageously provides that the sebum absorbing film is connected to a substrate in the edge portion, the substrate being cut out or transparent in the area of the film to be brought into contact with the skin surface. Such a collecting or measuring means makes sure that the sebum absorbing film is clamped and can be evaluated in a smooth state after application. In particular, an optical or opto-electronic evaluation using the transmitted light method is possible so that the evaluation can be performed with a high measuring accuracy, especially when using opto-electronic means. Here, it is essential that the surface of the sebum absorbing film is perfectly plane so that, upon evaluation, no focussing problems will occur that could falsify the measuring results.

The substrate may be annular in shape. Here, the substrate may be made of two rings clamping the sebum absorbing film between them.

The substrate may be made of a transparent rigid substrate film connected in the edge portion with the sebum absorbing film on the side of the film averted from the skin surface.

A non-adhesive transparent film may be arranged between the sebum absorbing film and the substrate. Such a film serves to support the sebum absorbing film.

At least the edge portion of the substrate surface facing away from the skin surface has an adhesive area. Thereby, the film can be fastened to a device for evaluating the sebum absorbing film.

The adhesive area of the substrate film may be provided with a protective film, e.g. of silicon material, whereby the adhesive area is protected prior to use.

Preferably, the at least one film has its edge portion welded ultrasonically to the substrate. Ultrasonic welding is advantageous in that no adhesive can influence the properties of the sebum absorbing film.

The substrate may be adhered by its adhesive area with a support frame adapted to an optical or opto-electronic evaluation means and having a cut out or transparent central area.

For example, it is possible to adhere the substrate with the sebum absorbing film onto a slide frame and to transfer it to an automatic evaluation wit this frame.

The following is a detailed description of embodiments of the invention taken in conjunction with the accompanying drawings.

DESCRIPTION OF THE PREFERRED EMBODIMENTS

Figure 1:
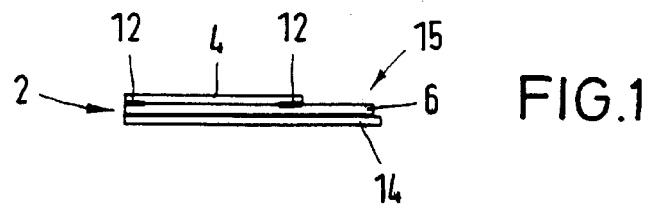
FIG. 1 is a cross section of a first embodiment of the present invention.

According to a first embodiment illustrated in FIG. 1, the collecting means or measuring means for determining the secretion of sebum from the skin is multi-layered and comprises a sebum absorbing outer film 4 connected at two opposite edge portions 12 with a substrate film 6 of a transparent rigid material, a protective film 14 with an adhesive layer 10, preferably provided on the protective film 14, is arranged on the side of the substrate film 6 averted from the film 4.

The sebum absorbing film 4 consists, for example, of a microporous hydrophobic polypropylene film with a porosity between 20 and 50%, a thickness between 20 and 30 μm and a pore size between 0.03 and 0.15 μm. Such a film has a uniform distribution of micropores and is opaque in its original state. Upon contact with sebum, the pores fill up, whereby the film becomes transparent at the corresponding places. Such a film is therefore suitable for various tests with respect to the secretion of sebum from the skin, if the film is brought into contact with the skin surface, possibly by applying a slight pressure.

The film 4 has its edge portions 12 welded, for example, by ultrasonic welding, to the substrate film 6, and it is held tight by the rigid substrate film 6. The substrate film 6 is flexible to a certain extent and allows the film 4 to be pressed onto the skin surface without the substrate film 6 kinking so that the film 4 can also be held tight for evaluation of the skin print and no measurement errors due to a non-planar film 4 can occur during evaluation.

The substrate film 6 may also be cut out in its central part, the cut-out delimiting a defined measuring area on the film 4. In this case, the substrate film 6 may also be made of a light impermeable material.

Figure 2:
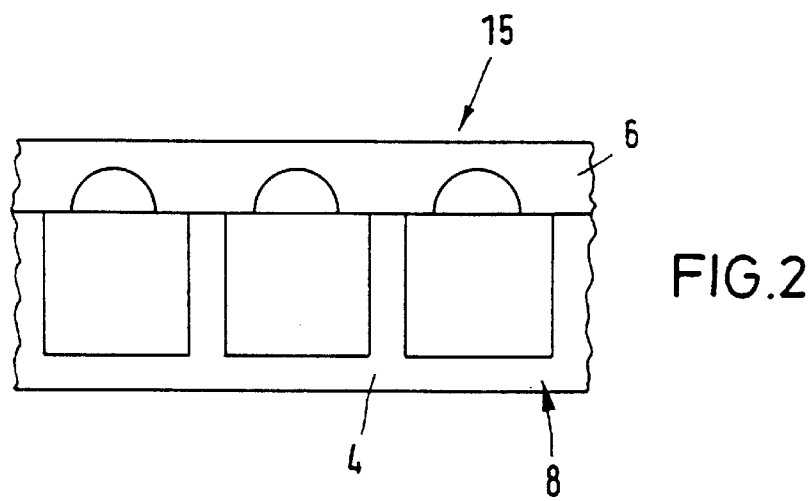
FIG. 2 illustrates a test strip.

FIG. 2 illustrates a test strip 8 with a plurality of measuring means for determining the secretion of sebum from the skin. The measuring means are prepared for removal by providing a punch cut in a correspondingly layered strip material and may easily be taken from the test strip 8.

Figure 3:
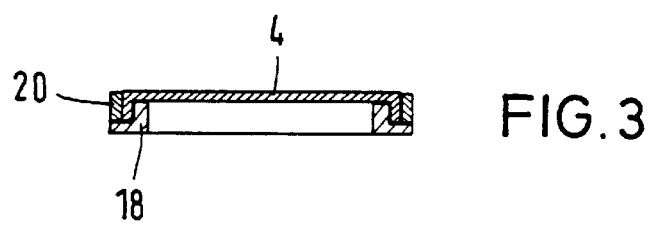
FIG. 3 is a cross section of a second embodiment.

FIG. 3 illustrates a second embodiment, wherein the sebum absorbing film 4 is tightened between two rings or frame portions 18, 20. Such rings keep the sebum absorbing film 4 tight and may also be adhered onto a support frame 22, using an adhesive layer in the side of the ring 18 averted from the film 4, so as to facilitate or automate the evaluation. The measuring means with the frame portions 18, 20 and the film 4 may of course be evaluated immediately without the support frame 22, be it optically or opto-electrically.

Figure 4:
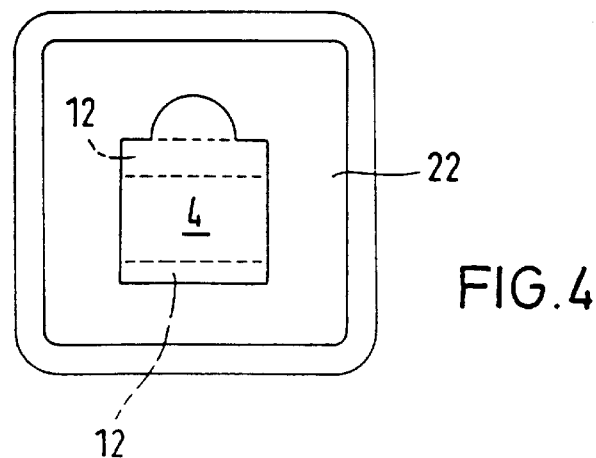
FIG. 4 illustrates a support frame for evaluating the film print.

FIG. 4 illustrates the support frame 22 together with a measuring means according to FIGS. 1 and 2. Here, the measuring means is preferably fastened by means of an adhesive layer at the support frame 22. Such a support frame 22 may be a standard slide frame.

Although a preferred embodiment of the invention has been specifically illustrated and described herein, it is to be understood that minor variations may be made in the apparatus without departing from the spirit and scope of the invention, as defined the appended claims.

I claim:

1. A device for collecting the secretion of sebum from the skin comprising a micorporous hydrophobic sebum absorbing opaque film (4) having a first side adapted to be pressed against skin surface to absorb sebum and an opposite second side with the light permeability of the opaque film being a measure of the absorbed sebum, said sebum absorbing film second side being connected to a substrate (2, 6, 18, 20) under tension such that said sebum absorbing film (4) is substantially tight, said substrate is cut out in an area of the sebum absorbing film (4) which is adapted to be brought into contact with skin surface, and said substrate (2, 6, 18, 20) including means (18, 20) for maintaining said sebum absorbing film (4) substantially tight whereby the sebum absorbing film (4) can be presses onto the skin surface without kinking and can be held tightly for evaluation thus avoiding measurement errors.

2. The collecting device as defined in claim 1 wherein the substrate maintaining means (18, 20) includes two frame parts (18, 20), and said sebum absorbing film (4) is gripped tight between said frame parts (18, 20).

3. The collecting device as defined in claim 1 wherein the substrate (2) and the sebum absorbing film (4) are of an annular configuration.

4. The collecting device as defined in claim 1 wherein the substrate maintaining means (18, 20) is a frame.

5. A device for collecting the secretion of sebum from the skin comprising a micorporous hydrophobic sebum absorbing opaque film (4) having a first side adapted to be pressed against skin surface to absorb sebum and an opposite second side with the light permeability of the opaque film being a measure of the absorbed sebum, said sebum absorbing film second side being connected to a substrate (2, 6, 18, 20) under tension such that said sebum absorbing film (4) is substantially tight, said substrate (2) includes a transparent portion in the area of the film (4) which is adapted to be brought into contact with skin surface, and said substrate (2, 6, 18, 20) including means (18, 20) for maintaining said sebum absorbing film (4) substantially tight whereby the sebum absorbing film (4) can be presses onto the skin surface without kinking and can be held tightly for evaluation thus avoiding measurement errors.

6. The collecting device as defined in claim 5 wherein the substrate maintaining means (18, 20) includes two frame parts (18, 20), and said sebum absorbing film (4) is gripped tight between said frame parts (18, 20).

7. The collecting device as defined in claim 5 wherein the substrate (2) and the sebum absorbing film (4) are of an annular configuration.

8. The collecting device as defined in claim 5 wherein the substrate maintaining means (18, 20) is a frame.

* * * * *